United States Patent [19]
Schroeppel et al.

[11] Patent Number: 5,957,966
[45] Date of Patent: Sep. 28, 1999

[54] IMPLANTABLE CARDIAC LEAD WITH MULTIPLE SHAPE MEMORY POLYMER STRUCTURES

[75] Inventors: Edward A. Schroeppel; Paul R. Spehr; James E. Machek, all of Lake Jackson, Tex.

[73] Assignee: Intermedics Inc., Angleton, Tex.

[21] Appl. No.: 09/025,164

[22] Filed: Feb. 18, 1998

[51] Int. Cl.⁶ ............................ A61M 25/00; A61N 1/05
[52] U.S. Cl. ........................ 607/122; 607/119; 607/128
[58] Field of Search ................................ 607/119, 122, 607/126, 128

[56] References Cited

U.S. PATENT DOCUMENTS

| | | |
|---|---|---|
| 4,882,777 | 11/1989 | Narula . |
| 5,423,772 | 6/1995 | Lurie et al. . |
| 5,462,545 | 10/1995 | Wang et al. . |
| 5,562,678 | 10/1996 | Booker . |
| 5,634,936 | 6/1997 | Linden et al. ........................ 606/213 |

*Primary Examiner*—William E. Kamm
*Assistant Examiner*—Carl H. Layno
*Attorney, Agent, or Firm*—John R. Merkling; Trop, Pruner, Hu & Miles, P.C.

[57] ABSTRACT

A cardiac lead is provided that is capable of deforming in situ to accommodate difficult myocardial structures. The lead includes a connector for coupling to a cardiac stimulator and a flexible tubular sleeve coupled to the connector. The sleeve is composed of a thermally-sensitive shape-memory polymeric material and is deformable in situ into a permanent shape. An electrode is coupled to the sleeve and a conductor wire is coupled to the connector and to the first electrode.

32 Claims, 9 Drawing Sheets

IMPLANTABLE CARDIAC LEAD WITH MULTIPLE SHAPE MEMORY POLYMER STRUCTURES

BACKGROUND OF THE INVENTION

1. Field of the Invention

The present invention relates generally to implantable medical devices, and more particularly to a cardiac lead incorporating a sleeve composed of a shape-memory polymeric material capable of deforming following implantation into the body.

2. Description of the Related Art

Implantable tubular structures, such as catheters, cardiac stimulator leads, shunts, and others are presently used for a variety of diagnostic and therapeutic purposes. The particular shape indicated for a given implantable tubular structure is dictated in large part by the anticipated physiological structures that will be encountered by the structure. For example, an endocardial lead attached distally to the ventricular apex may have a relatively straight shape. However, other situations may call for a more particularly shaped implantable tubular structure. For example, cardiac stimulator leads intended for implantation in the right atrium or coronary sinus are advantageously provided with one or more bends in the tubular structure to either facilitate entry of the tubular structure into an obliquely disposed passageway, such as the coronary sinus, or to enable the tubular structure to conform with and thereby engage the internal structure of the right atrium to anchor the tubular structure in a particular position.

Presently, some effort is made by medical device manufacturers to supply implantable tubular structures with preselected shapes intended to accommodate particularized physiological structures. These commercially available devices are often supplied in different lengths, and with a variety of different types of preestablished bends. The sizes and preestablished shapes of these conventional devices are typically based on some empirically determined norm for the size and shape of the average anatomical structure to be encountered by the implantable device. The disadvantage associated with using conventional off-the-shelf implantable tubular devices is that internal anatomy varies greatly among individual patients and these systems cannot be deformed in situ. For this reason, a cardiac stimulator lead that may fit one patient may not be suitable for another patient. For those patients whose internal anatomy differs significantly from the hypothetical norm, the use of an off-the-shelf implantable tubular device may represent a compromise that, while not necessarily life threatening, may nevertheless involve a less than optimal treatment regimen.

For example, some patients present serious arrhythmia conditions that stem from highly localized electrical disruptions in the left side of the heart. In some of these cases, epicardial or right ventricular endocardial cardiac stimulation may not provide electrical stimulation that is localized enough to treat the arrhythmia; endocardial stimulation via the coronary sinus may be indicated. Regardless of the ultimate endocardial site requiring stimulation, an endocardial cardiac stimulator lead is normally implanted into the heart by passing a lead through the superior vena cava and into the right atrium. The pathway from the superior vena cava to the right atrium is relatively straight. However, the coronary sinus ostium is located approximately at a 90° angle from that straight pathway. If coronary sinus implantation is indicated, the lead must negotiate the 90° turn to successfully enter the coronary sinus ostium. If the ultimate implantation site for the tip of the lead is within one of the tributaries of the great cardiac vein, the lead must undergo one or possibly several more substantial changes in direction before reaching the targeted tissue site. A conventional lead with permanent bends may prove difficult to navigate to the targeted tissue site under such conditions. There are numerous examples of other types of anatomical structures where such significant changes in direction are associated with the implantation pathway.

One conventional device for imparting a bend in a catheter incorporates a bellows joint for establishing the bent shape. The capability of this system to customize an implantable tubular device is limited in several aspects. First, the types of shapes that may be imparted are normally limited to two dimensions. Second, the portion of the catheter that may be shaped is limited to the immediate vicinity of the bellows joint.

Another conventional lead system employs a mechanical linkage between the lead tip and the proximal end of the lead to enable the lead tip to be selectively curved or straightened by hand manipulating a stylet-like handle connected proximally to the linkage. This system provides a limited ability to manipulate the position of the lead tip in situ. However, the system is complex, costly to manufacture, and because of the space requirements of the linkage, presents a lower limit to the minimum possible outer diameter for the lead.

The present invention is directed to overcoming or reducing one or more of the foregoing disadvantages.

SUMMARY OF THE INVENTION

In accordance with one aspect of the present invention, a cardiac lead is provided. The cardiac lead includes a connector for coupling to a cardiac stimulator and a flexible tubular sleeve coupled to the connector. The sleeve is composed of a thermally-sensitive shape-memory polymeric material and is deformable in situ into a permanent shape. A first electrode is coupled to the sleeve. A conductor wire is coupled to the connector and to the first electrode.

In accordance with another aspect of the present invention, a cardiac lead is provided. The cardiac lead includes a connector for coupling to a cardiac stimulator and a flexible tubular sleeve coupled to the connector. The sleeve has a first segment composed of a thermally-sensitive shape-memory polymeric material and a second segment of a non-shape-memory polymeric material. The first segment is deformable in situ into a first permanent shape. A first electrode is coupled to the sleeve. A conductor wire is coupled to the connector and to the first electrode.

In accordance with still another aspect of the present invention, a cardiac lead is provided. The cardiac lead includes a connector for coupling to a cardiac stimulator and a flexible tubular sleeve coupled to the connector. The sleeve has a first segment composed of a thermally-sensitive shape-memory polymeric material and a second segment disposed over and coupled to the first segment. The second segment is composed of a thermally-sensitive shape-memory polymeric material. The first and second segments are deformable in situ into a first permanent shape and second permanent shape. A first electrode is coupled to the sleeve and a conductor wire is coupled to the connector and to the first electrode.

In accordance with still another aspect of the present invention, a cardiac lead is provided. The cardiac lead includes a connector for coupling to a cardiac stimulator and a flexible tubular sleeve coupled to the connector that has a lumen. The sleeve is composed of a thermally-sensitive shape-memory polymeric material and is deformable in situ into a permanent shape. A first electrode is coupled to the sleeve. A conductor wire is coupled to the connector and to the first electrode. A stylet is removably disposed in the lumen. The stylet is adapted to transfer heat to the sleeve in situ.

BRIEF DESCRIPTION OF THE DRAWINGS

The foregoing and other advantages of the invention will become apparent upon reading the following detailed description and upon reference to the drawings in which.

DETAILED DESCRIPTION OF SPECIFIC EMBODIMENTS

Figure 1:
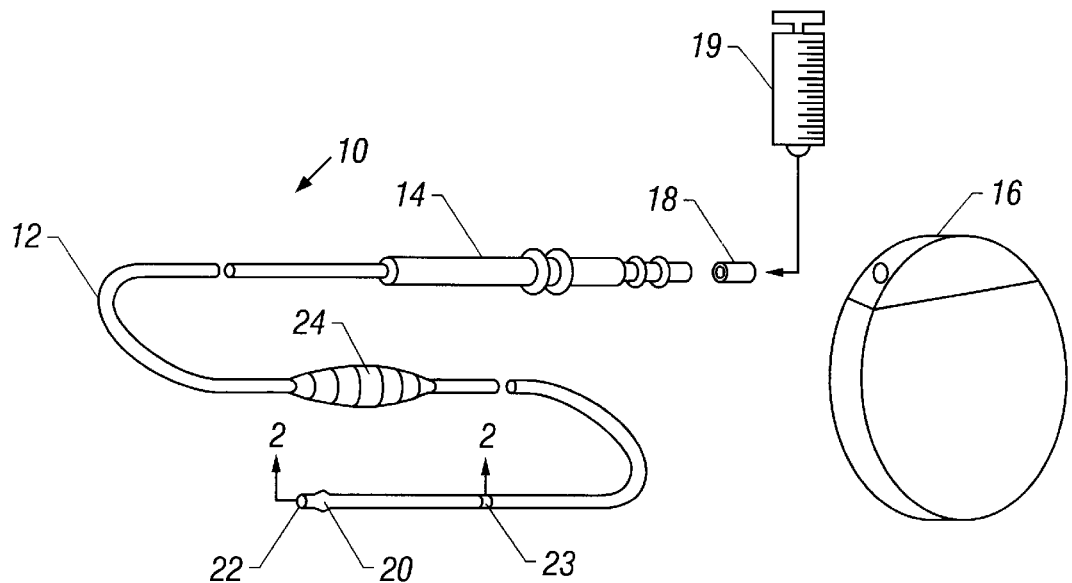
FIG. 1 is a pictorial view of an exemplary embodiment of a cardiac lead and a cardiac stimulator in accordance with the present invention.

In the drawings described below, reference numerals are generally repeated where identical elements appear in more than one figure. Turning now to the drawings, and in particular to FIG. 1, there is shown an exemplary cardiac lead 10 that includes a flexible insulating sleeve 12 that is coupled proximally to a connector 14. The connector 14 is designed to be inserted into a cardiac stimulator 16, and is shown highly exaggerated in size relative to the cardiac stimulator 16. The cardiac stimulator 16 may be a pacemaker, a cardioverter/defibrillator, or other type of stimulator or a sensing instrument. An adaptor 18 is provided that may be coupled to the connector 14. The adaptor 18 is designed to enable a syringe 19 to be coupled to the connector 14 so that heating or cooling fluid may be injected into the lead 10 as described more below. The illustrated embodiment of the lead 10 is bipolar. Accordingly, the distal end 20 of the sleeve 12 is provided with a tip electrode 22 and another electrode 23 located proximal to the tip electrode 22. However, unipolar arrangements are possible as well. A suture sleeve 24 is slipped over the sleeve 12. During implantation, the suture sleeve 24 is sewn to the vascular wall at the site of transvenous entry.

Figure 2:
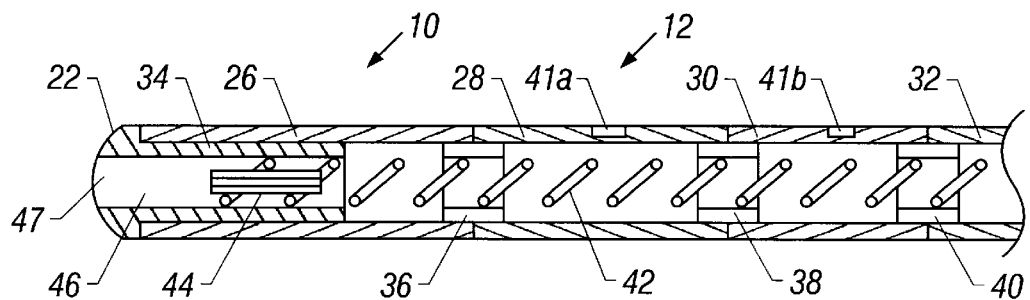
FIG. 2 is a sectional view of the cardiac lead of FIG. 1 taken at section 2—2 in accordance with the present invention.

The detailed structure of the sleeve 12 may be understood by referring now to FIG. 2, which is a cross-sectional view of FIG. 1 taken at section 2—2. The sleeve 12 is subdivided into individual segments 26, 28, 30, and 32. The segment 26 is slipped over the proximal end 34 of the tip electrode 22 and secured thereto by a suitable medical grade adhesive, such as silicone adhesive. The segment 26 may be composed of a suitable biocompatible polymeric material, such as silicone, polyurethane, or like materials. The segment 26 is coupled to the segment 28 by means of a cylindrical joint tube 36 that is dimensioned to have an outer diameter that is approximately equal to the inner diameter of the segments 26 and 28. The opposing ends of the segment 26 and the segment 28 are slipped over and secured to the joint tube 36 by a suitable medical grade adhesive, such as silicone, the two-part adhesive Polycin/Vorite supplied by CasChem, Inc., or similar adhesives. The segment 28 is coupled to the segment 30, and the segment 30 is, in turn, coupled to the segment 32 in like fashion via joint tubes 38 and 40. The joint tubes 36, 38, and 40 may be fabricated from a variety of biocompatible materials, such as stainless steel, titanium, or polyurethane, or other suitable materials. If a polymeric material such as polyurethane is used, the material should be fabricated with a sufficient hardness so that when the opposing ends of two adjoining segments, such as 26 and 28, are slipped over the joint tube 36, the joint tube 36 does not collapse. Accordingly, it is anticipated that a polyurethane joint tube, such as 36, should have a Durometer value of 80 D or greater.

The segments 28 and 30 may be provided with respective radiographic markers 41a and 41b to enable the implanting physician to determine the position of the segments 28 and 30 during implantation via fluoroscopy, angiography or other imaging techniques. The markers 41a and 41b may be composed of a suitable biocompatible radiopaque material, such as stainless steel, titanium, tantalum or like materials.

The lead 10 is provided with a conductor wire 42 that is connected proximally to the connector 14 shown in FIG. 1 and distally to the tip electrode 22. The connection between the conductor wire 42 and the tip electrode 22 is via a cylindrical crimp tube 44 that is disposed inside the lumen 46 of the tip electrode 22. The conductor wire 42 is wrapped around the exterior of the crimp tube 44 and the proximal end of the tip electrode is swaged to secure the conductor wire 42 in place. Another conductor wire (not shown) couples the electrode 23 shown in FIG. 1 to the connector 14. The conductor wire 42 is depicted as a single individually insulated wire. However, the person of ordinary skill in the art will appreciate that the conductor wire may not be individually insulated if the lead 10 is unipolar or if the various conductor wires in the lead 10 are coaxially arranged or arranged in a nested configuration.

The tip electrode 22 and the electrode 23 may be fabricated from a variety of biocompatible conducting materials, such as titanium, stainless steel, iridium oxide coated titanium, or other suitable materials. The tip electrode 22 is provided with an orifice 47 to enable the passage of fluid as discussed below.

Figure 3:
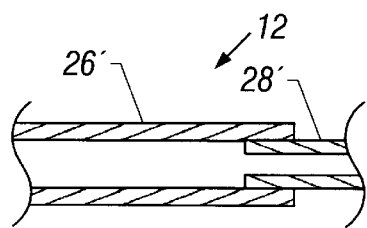
FIG. 3 is a cross-sectional view like FIG. 2 of an alternate embodiment of the cardiac lead in accordance with the present invention.
Figure 4:
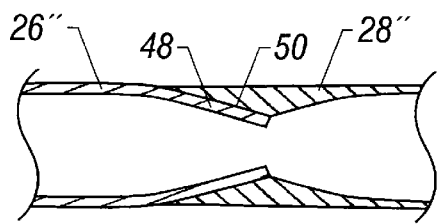
FIG. 4 is a cross-sectional view like FIG. 2 of another alternate embodiment of the cardiac lead in accordance with the present invention.

Alternative structures may be employed to join two adjoining segments of the sleeve 12. FIG. 3 is a cross-sectional view from the same perspective as FIG. 2, but focused on the attachment between adjoining segments 26 and 28, now designated, respectively, 26' and 28'. The segment 26' is fabricated with an inner diameter that is just larger than the outer diameter of the segment 28' so that the segment 28' may be slipped inside the segment 26' and secured thereto by means of a suitable medical grade adhesive of the type described above. In another alternate embodiment depicted in FIG. 4, the segment, now designated 26" is fabricated with a tapered exterior 48 and the segment, now designated 28", is fabricated with a mating tapered female surface 50 that permits the segment 26" and the segment 28" to be joined with a relatively isodiametric profile.

Referring again to FIG. 2, the segments 28 and 30 are designed to be selectively deformable in situ into preselected shapes to enable the lead 10 to conform to particular physiological structures. In this regard, the segments 28 and 30 are advantageously composed of a thermally-sensitive shape-memory polymeric material. A heat-sensitive shape-memory polymer behaves generally like a rigid material while at temperatures below the glass transition temperature $T_g$, but undergoes significant softening and may be readily plastically deformed when heated above $T_g$. When the material is then cooled below $T_g$, the deformation is fixed and the shape remains stable. However, the original shape of the material may be recovered by reheating the material above $T_g$.

During production, the segments 28 and 30 are first molded into a permanent shape. A variety of well known molding techniques may be used to create the segments 28 and 30, such as injection molding, extrusion molding, or like techniques. The molding process subjects the heat-sensitive shape-memory polymeric material to a temperature well in excess of the $T_g$ for the material for a sufficient time to form the segments 28 and 30 with their permanent shapes. Thereafter, the segments 28 and 30 may be deformed into temporary shapes by deforming the segments 28 and 30 at a temperature above $T_g$, and maintaining the segments 28 and 30 in the temporary shapes while the temperature is lowered below $T_g$. After cooling below $T_g$, the segments 28 and 30 retain the temporary shapes. However, if the segments 28 and 30 are later heated above $T_g$, they will deform substantially back into the permanent shapes in which they were originally molded. In this way, the segments 28 and 30 may be initially produced with permanent shapes that will enable the lead 10 to more readily conform to particular physiological structures within the heart. Prior to implantation, the segments 28 and 30 may be heated above $T_g$ and deformed to a temporary shape, such as the straight shape shown in FIG. 2, that is more suitable for transvenous insertion. When a heart structure is encountered that requires a bend in the lead 10, one or both of the segments may be heated above $T_g$ so that the segments 28 and 30 return substantially to their permanent shapes, thereby changing the shape of the lead to more readily conform to the heart structure.

Where molding of the desired permanent shape is difficult in view of the molding process used and the small dimensions of the segments 28 and 30, the segments 28 and 30 may be molded with a first permanent shape that best suits the molding process. This may be a straight shape. Thereafter, the segments 28 and 30 may be provided with a new permanent shape by heating the segments 28 and 30 above $T_g$, deforming the segments 28 and 30 into a new desired permanent shape, (e.g. a shape that suits the anticipated heart structure), and maintaining the segments 28 and 30 in that shape and at that temperature for a selected period of time. The heating time required to set the new permanent shape will depend on the particular polymer.

The segments 28 may be composed of heat-sensitive shape-memory polymeric materials that have the same $T_g$. When heated above $T_g$, the segments 28 and 30 will deform substantially to their permanent shapes at the same time. However, the segments 28 and 30 may be advantageously fabricated with different glass transition temperatures so that the segments 28 and 30 may be deformed in situ in stages. In this way, the segment 30 may be deformed in situ to facilitate the passage of the lead through a first heart structure. Later in the implantation procedure, the segment 28 may be deformed to facilitate passage of the lead 10 through another structure in the heart.

Figure 5:
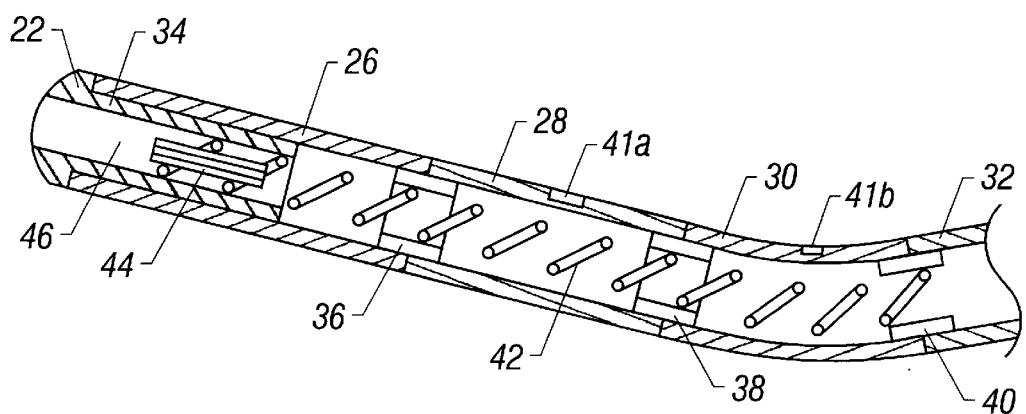
FIG. 5 is a cross-sectional view like FIG. 2 depicting in situ deformation of a segment of the cardiac lead in accordance with the present invention.

For the purpose of illustration, assume that the segment 30 has a glass transition temperature $T_{g1}$ and the segment 28 has a glass transition temperature $T_{g2}$ that is higher than $T_{g1}$. In addition, assume that the segments 28 and 30 are molded at the time of fabrication into the straight configurations depicted in FIG. 2, and thereafter provided with the curved permanent shapes shown in FIG. 6. A relatively straight lead is better suited for the initial stages of transvenous implantation, such as the initial transvenous entry and navigation from the introduction vessel to the superior vena cava. Accordingly, subsequent to the establishment of the permanent shapes shown in FIG. 6 and before implantation, the segments 28 and 30 are heated above their respective glass transition temperatures, deformed into the straightened configurations depicted in FIG. 2, and cooled below their respective glass transition temperatures, $T_{g1}$ and $T_{g2}$. The segments 28 and 30 retain the temporary shape depicted in FIG. 2. As shown in FIG. 5, if the segment 30 is again heated above the glass transition temperature $T_{g1}$, the segment 30 returns substantially to the bent configuration shown in FIG.

Figure 6:
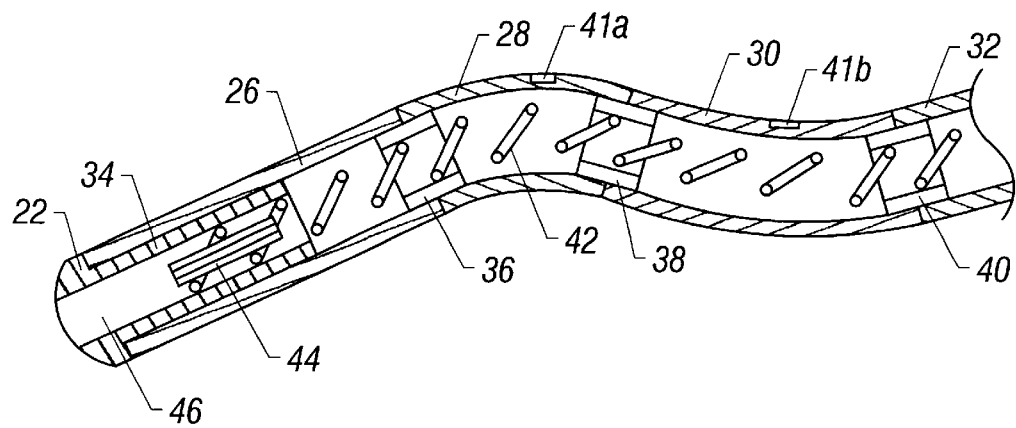
FIG. 6 is a cross-sectional view like FIG. 2 depicting in situ deformation of another segment of the cardiac lead in accordance with the present invention.

5. Similarly, as shown in FIG. 6, if the temperature of the segment 28 is then raised above $T_{g2}$, the segment 28 returns substantially to the bent configuration shown.

Figure 7:
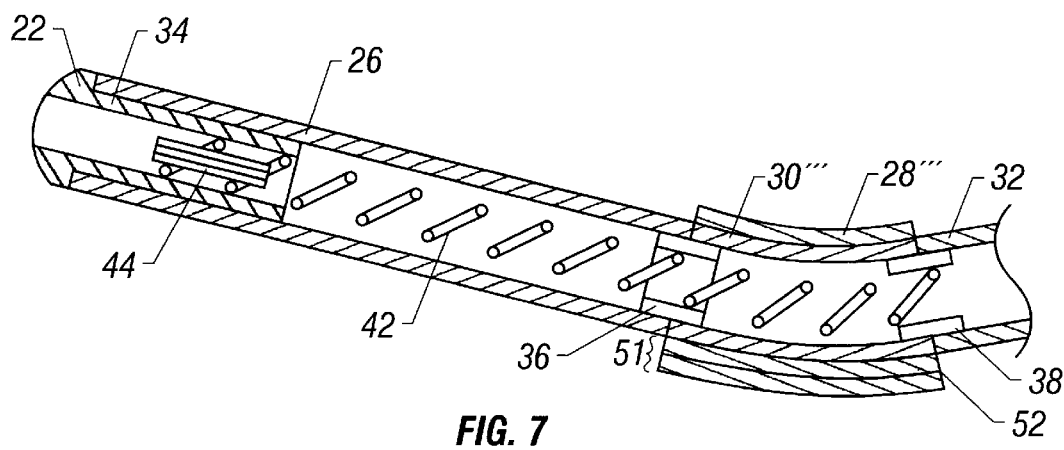
FIG. 7 is a cross-sectional view like FIG. 2 depicting an alternate embodiment of the cardiac lead incorporating two nested segments with one of the segments deformed in situ in accordance with the present invention.
Figure 8:
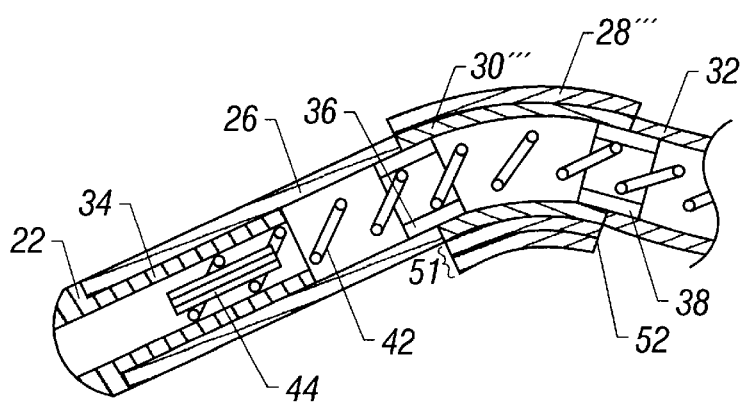
FIG. 8 is a cross-sectional view like FIG. 2 depicting the embodiment of FIG. 7 with the other of the segments deformed in situ in accordance with the present invention.
Figure 9:
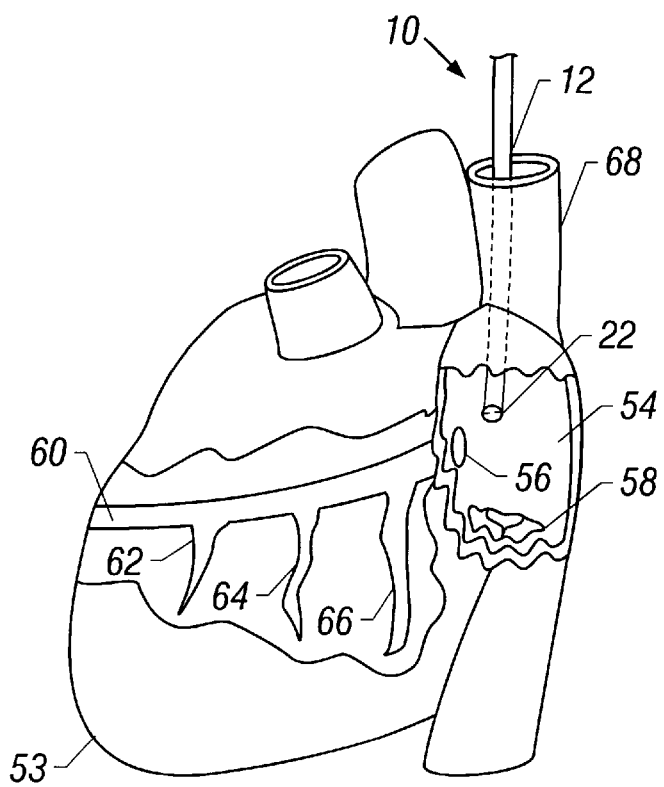
FIG. 9 is a posterior view of a human heart depicting initial insertion of the cardiac lead into the heart in accordance with the present invention.
Figure 10:
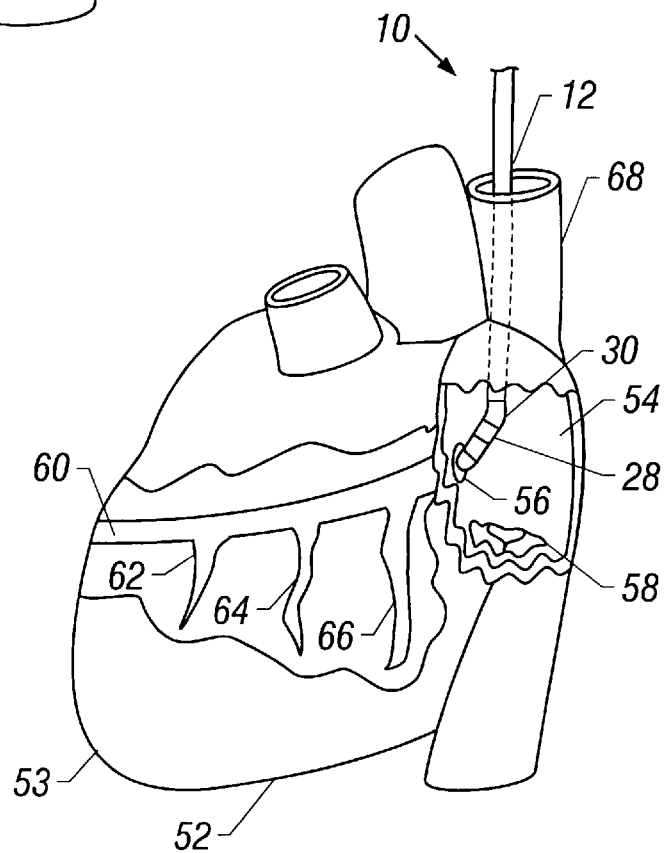
FIG. 10 is a view like FIG. 9 depicting entry of the cardiac lead into the coronary sinus ostium in accordance with the present invention.

In an alternate embodiment of the lead 10 depicted in FIGS. 7 and 8, the segments, now designated, respectively, 28''' and 30''', are assembled in a nested arrangement that also permits the sleeve, now designated 12', to assume multiple shapes in situ. The segment 28''' is slipped over and secured to the segment 30''' by a suitable medical grade adhesive of the types described above. FIG. 7 depicts the segment 30''' following elevation above $T_{g1}$ and deformation into the bent permanent shape shown. FIG. 8 depicts the bending of the segment 28''' following elevation of the temperature above $T_{g2}$. For the purpose of illustration, the segment 28''' is provided with a permanent shape that is arcuate in a direction opposite to the bend of the segment 30'''. In this nested arrangement, the shape-memory effect of the segment 28''' must be strong enough to bend the segment 30''' backwards into the shape shown in FIG. 8. This is accomplished by fabricating the segment 28''' with a larger thickness at the side designated 51. The excess material at the side 51 provides an enhanced bending stress to bend back the segment 30'''. Enhanced bending may also be accomplished by fitting the segment 28 with an elongated rib 52 composed of a shape-memory polymeric material.

Referring again to FIG. 2, it is desirable to heat the segments 28 and 30 in situ. This may be accomplished by introducing a heated fluid into the lumen 46 via the syringe 19 coupled to the adaptor 18 shown in FIG. 1. The orifice 47 permits the heated fluid to flow through the lumen 46 past the segments 28 and 30 and out the orifice 47 into the body. The heated fluid should be a biocompatible, body absorbable fluid, such as, for example, saline, alcohol, or like fluids. Other heating methods may be employed as discussed below.

The materials selected for the segments 28 and 30 should have glass transition temperatures that are above the anticipated maximum body temperature so that they do not soften and deform into undesirable shapes after implantation. Normal body temperature usually falls within the range 36to 37° C. However, a body subjected to high fever may reach about 42° C., so a $T_{g1}$ or $T_{g2} \geq 42°$ C. should ensure that the segments 28 and 30 do not undergo undesirable deformation after implantation.

For long-term implantation, the segments 28 and 30 may be fabricated from heat-sensitive shape memory polymers such as polynorbornene supplied by Nippon Zeon of Japan, polyurethane supplied by Mitsubishi Heavy Industries of Japan, Calo.Mer™ supplied by Polymer Technology Group of California, or similar materials. If the lead 10 is designed for more transient implantation, materials such as polyvinyl chloride, or similar materials may be used in addition to the above-described materials. Metallic materials, such as, for example, Nitinol, or similar materials coated with biocompatible polymeric materials, such as polyurethane may also be used. Strength may be added to the sleeve segments 28 and 30 by mixing fibers, such as fiberglass, or similar materials, with the material forming the segments 28 and 30.

The capability of bending the lead 10 into multiple arcuate shapes in situ may be exploited to permit the lead 10 to navigate difficult structures within the heart. In this regard, an exemplary implantation procedure is depicted in FIGS. 9, 10, 11, and 12. FIGS. 9, 10, 11, and 12 depict posterior views of a human heart 53 with the posterior side of the right atrium 54 shown cut away to reveal the coronary sinus ostium 56 and the tricuspid valve 58. A portion of the posterior of the myocardium 53 is cut away to reveal the great cardiac vein 60 and three tributaries, 62, 64, and 66 of the great cardiac vein 60. For the purpose of this illustration, the fixation point for the lead 10 is the tributary 64. The lead 10 is prepared for implantation by introducing the temporary straight shapes into the segments 28 and 30 shown in FIG. 2. The relatively straight lead 10 is then introduced into the superior vena cava 68 by conventional transvenous implantation methods. The lead 10 is advanced until the tip electrode 22 is positioned proximate the coronary sinus ostium 56. The temperature of the segment 30 is then raised above the glass transition temperature $T_{g2}$ by injecting the lumen 46 with heated fluid, and the segment 30 deforms substantially to the permanent bent shape shown in FIG. 10 and in FIG. 5. The lead 12 is now suitably shaped to readily enter the coronary sinus ostium 56.

Figure 11:
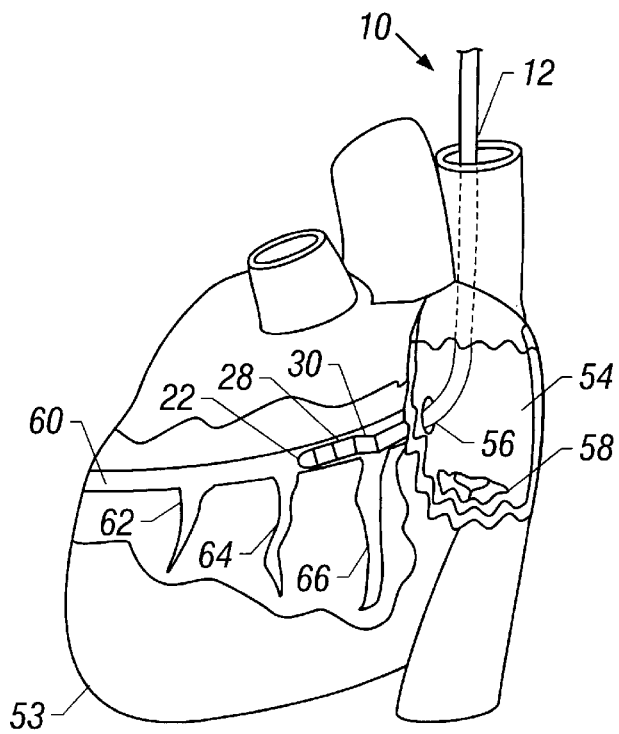
FIG. 11 is a view like FIG. 9 depicting movement of the cardiac lead into the great cardiac vein in accordance with the present invention.
Figure 12:
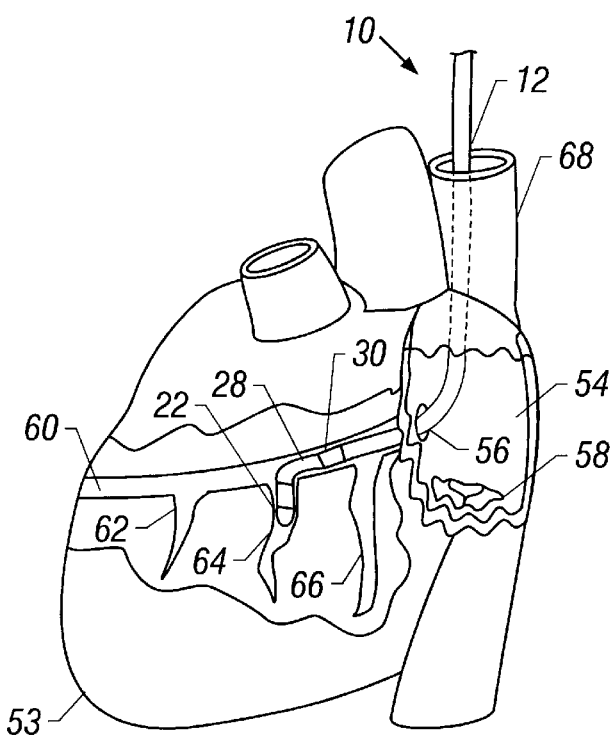
FIG. 12 is a view like FIG. 9 depicting entry of the cardiac lead into a tributary of the great cardiac vein in accordance with the present invention.

Referring now to FIG. 11, the lead 10 is advanced into the great cardiac vein 60 until the tip electrode 22 is proximate the fork between the great cardiac vein 60 and the tributary 64. When the tip electrode 22 is positioned at or near the opening to the tributary 64, the temperature of the segment 28 is elevated above the glass transition temperature, $T_{g2}$, again by injection of heated fluid. The segment 28 returns substantially to the permanent shape depicted in FIG. 6. Referring now to FIG. 12, the lead 10 may be readily advanced so that the tip electrode 22 may be positioned in the tributary 64 where desired.

Figure 13:
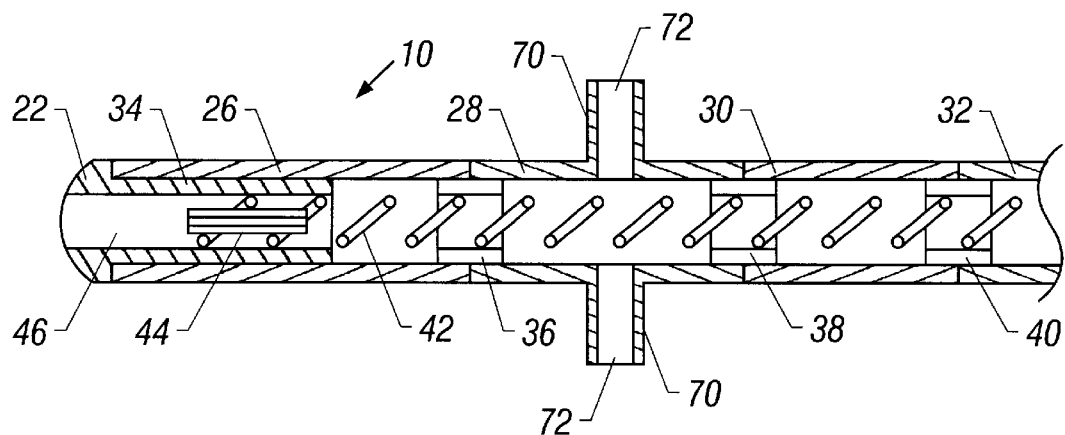
FIG. 13 is a cross-sectional view like FIG. 2 of an alternate embodiment of the cardiac lead incorporating hollow moveable tines in accordance with the present invention.
Figure 14:
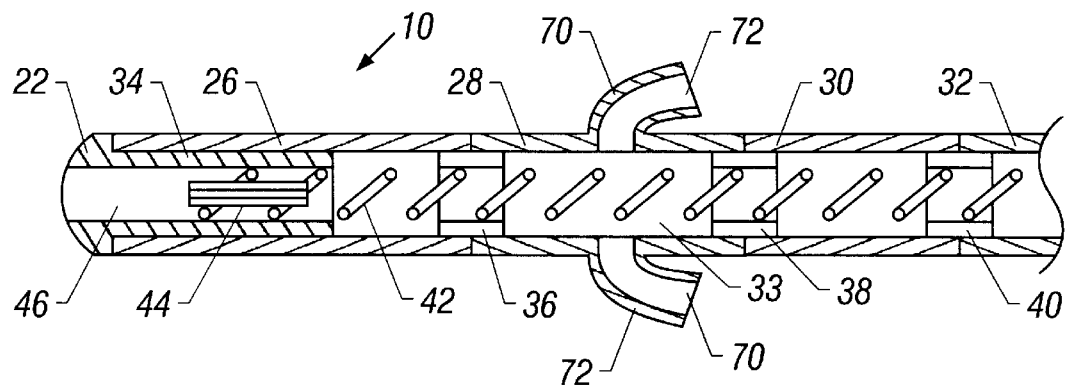
FIG. 14 is a cross-sectional view like FIG. 13 depicting the tines prior to in situ deformation in accordance with the present invention.

The lead 10 may be provided with structure to secure the sleeve 12 to myocardial tissue and to facilitate tissue ingrowth. As shown in FIGS. 13 and 14, the lead 10 may be provided with one or more radially projecting tines 70 composed of a shape-memory polymeric material and either integrally molded with one of the segments, e.g. 28, as shown in FIGS. 13 and 14 or coupled to the sleeve 12 as a separate structure. The tines 70 may be fabricated with a radially projecting permanent shape depicted in FIG. 13. Prior to implantation, the tines 70 may be bent into the swept-back temporary shape shown in FIG. 14 that provides a more streamlined profile for implantation through narrow structures. When the tip electrode 22 is positioned at the desired site, the temperature of the tines 70 may be elevated above the glass transition temperature by heated fluid injection so that the tines 70 return to the fully extended position shown in FIG. 13.

Where heated fluid is used to heat the tines 70, a flow path may be established from the lumen 46. Each tine 70 is provided with a lumen 72 that extends from the lumen 46 of the sleeve 12 and terminates at the tip of the tine 70. The lumens 72 also serve as favorable sites for tissue ingrowth.

Figure 15:
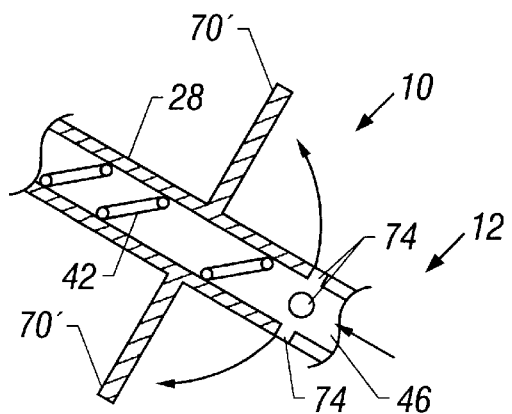
FIG. 15 is a cross-sectional view like FIG. 14 of an alternate embodiment of the cardiac lead incorporating solid moveable tines in accordance with the present invention.

Alternative structures and methods may be employed to heat a given set of tines, as well as the segments 28 and 30, above the glass transition temperature. FIG. 15 is a cross-sectional view of the segment 28 depicting an alternative arrangement for the tines, now designated 70'. In this embodiment, the tines 70' are fabricated as solid structures and the segment 28 is provided with one or more passages 74 that are positioned proximally to the tines 70'. Heated fluid introduced into the lumen 46 exits the passages 74 following the flow path indicated by the arrows. As a result, the tines 70' are bathed in a stream of heated fluid so that the temperature of the tines 70' may exceed the glass transition temperature and the tines then assume the permanent position depicted in FIG. 15.

Selectively moveable tines may be advantageously employed in situations where it is desirable for the electrodes 22 and 23 shown in FIGS. 1, 13 and 14 to function as floating electrodes. For example, the lead 10 may be implanted in the right atrium to both sense atrial depolarizations and pace the right atrium. The capture of the right atrium by atrial pacing is achieved by the use of simultaneously occurring pulses having opposite phases with respect to a reference anode. One electrode, such as the tip electrode outputs a voltage, +V, and the other electrode 23 outputs a voltage, −V, at the same time. Satisfactory performance of the lead 10 relies on blood in the atrium to carry the signal currents and requires the electrodes to be physically separated from surrounding solid tissues, preferably by 2 cm or more. To achieve such large minimum spacing, tines in excess of 2 cm in length may be necessary. Conventional leads with conventional fixed tines of such long lengths would be extremely difficult to implant transvenously. However, the tines 70 depicted in FIGS. 13 and 14 may be swept back prior to implantation to yield a more isodiametric profile that is better suited to passage through vessels, such as the superior vena cava. When positioned in the right atrium, the tines 70 may be unfolded as described above.

Figure 16:
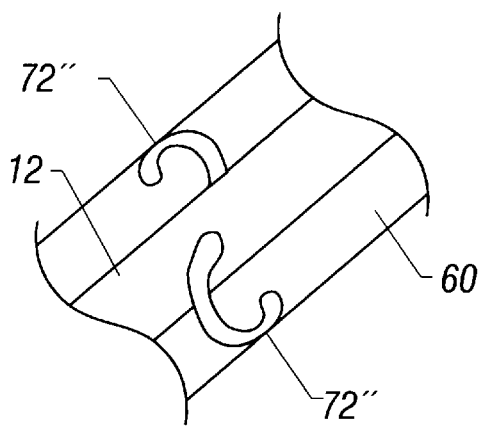
FIG. 16 is a pictorial view of an alternate embodiment of the cardiac lead incorporating moveable hook-shaped tines in accordance with the present invention.

As shown in FIG. 16, the tines, now designated 72", may be provided with a hook-shaped permanent shape. This arrangement may be advantageous where compliant, non-abrading contact with surrounding tissues, such as the walls of the great cardiac vein 60, is desirable.

Figure 17:
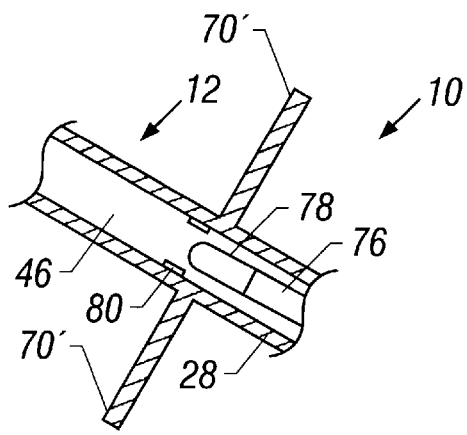
FIG. 17 is a cross-sectional view like FIG. 14 depicting insertion of a heated stylet in accordance with the present invention.
Figure 18:
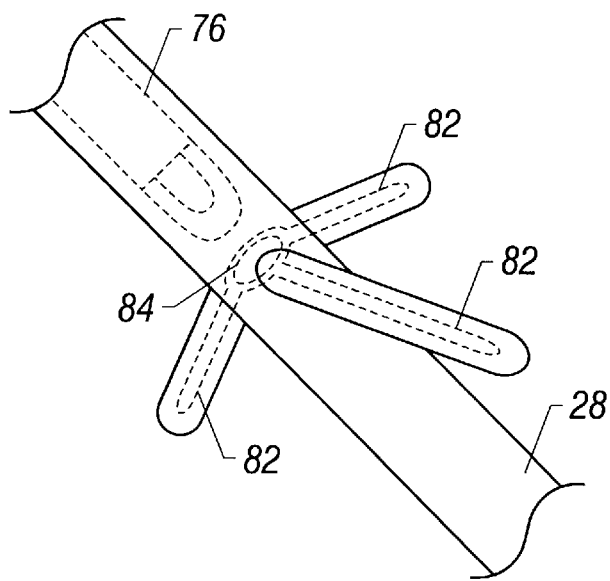
FIG. 18 is a pictorial view of the cardiac lead of FIG. 15 depicting incorporation of thermally conducting filaments into the tines in accordance with the present invention.

In another alternative arrangement depicted in FIG. 17, the tines 70' are heated above the glass transition temperature by means of a heated stylet 76 that is introduced into the lumen 46 and moved longitudinally until the tip 78 of the heated stylet 76 is near the tines 70'. The sleeve 12 may be fitted with an annular member 80 positioned distal to the tines 70' that acts as a stop to prevent the stylet tip 78 from moving substantially past the tines 70'. As shown in FIG. 18, the thermal conductivity of the tines 70' may be enhanced by providing each tine 70' with a thermally conducting filament 82, shown in phantom. The thermally conducting filaments 82 are joined proximally by an annular member 84 that serves a dual purpose of providing a thermally conducting pathway from the heated stylet 76 to the thermally conducting filaments 82, and serves as a stop for the stylet 76.

Figure 19:
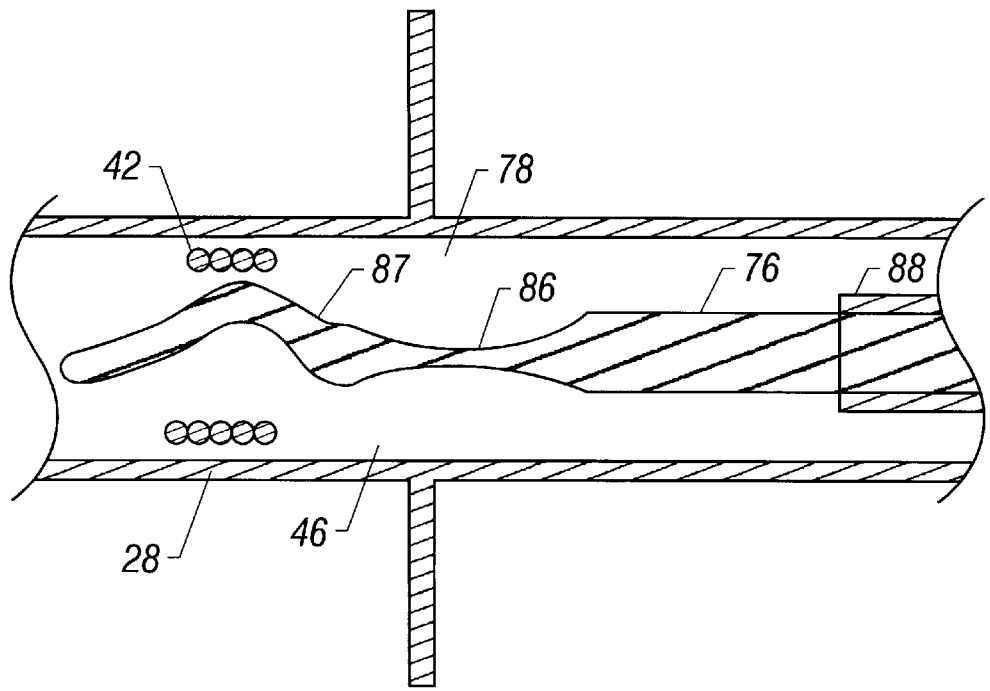
FIG. 19 is a detailed cross-sectional view of an exemplary embodiment of the heated stylet inserted into the cardiac lead in accordance with the present invention.
Figure 20:
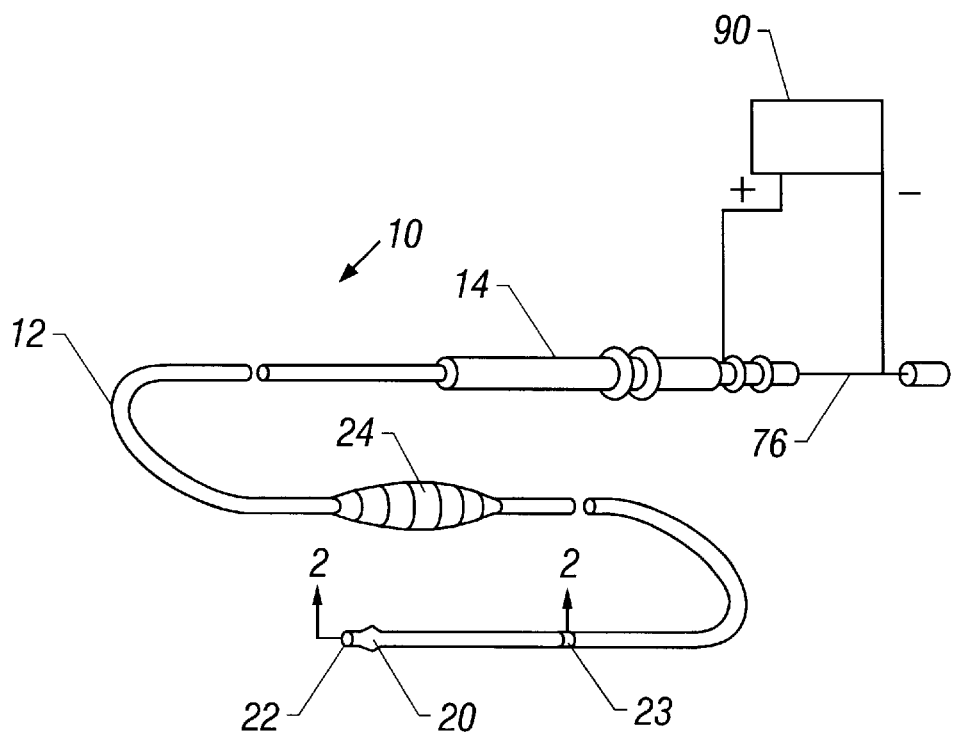
FIG. 20 is a pictorial of the cardiac lead depicting insertion of the stylet and connection of a voltage source to the stylet in accordance with the present invention.

The detailed structure of an exemplary embodiment of the stylet 76 suitable for use with a lead incorporating a conductor wire 42 that is not individually insulated may be understood by referring now to FIGS. 19 and 20. FIG. 19 is a cross-sectional view of the distal end of the stylet 76 and shows the tip 78. FIG. 20 is a pictorial view of the lead 10 and the stylet 76. The stylet 76 is advantageously composed of an electrically conducting material, such as stainless steel, titanium, or similar suitable materials coated with an electrically insulating coating 88. Near the tip 78, the stylet 76 is provided with a tapered portion 86 and an arcuate portion 87 not covered by the coating 88. The tapered portion 86 will more readily dissipate $I^2R$ losses when current is passed through the stylet 76 as a result of the diminished cross-sectional area. A voltage source 90 is coupled to the proximal end of the stylet 76 and the connector 14. The arcuate 87 portion of the stylet 76 contacts the conductor wire 42 to complete the circuit.

Figure 21:
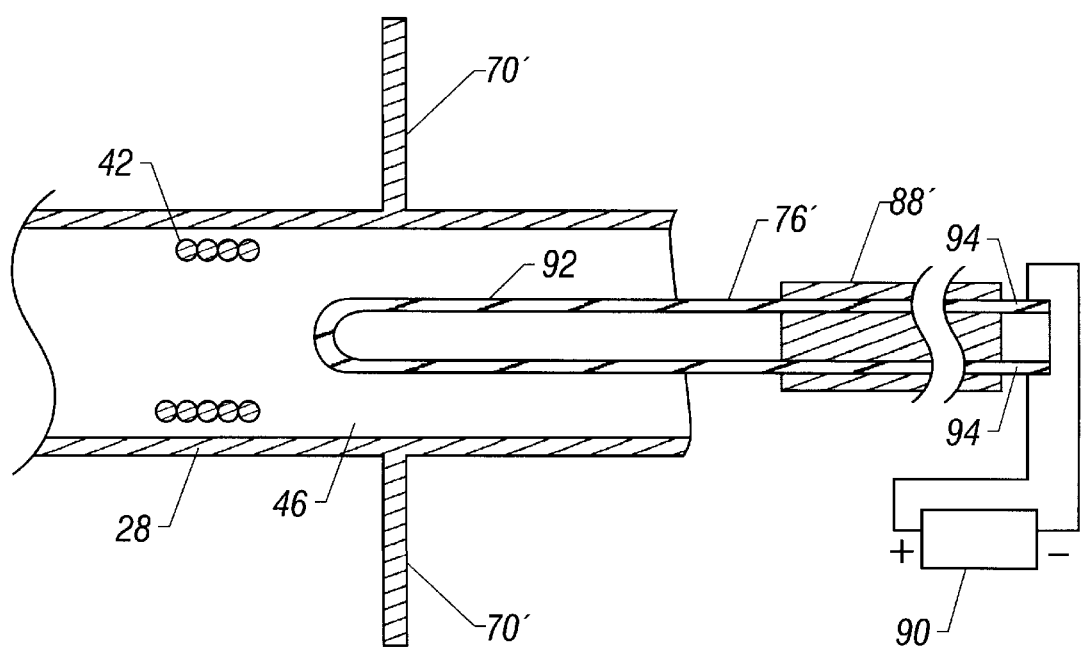
FIG. 21 is a cross-sectional view like FIG. 19 of an alternate embodiment of the stylet coupled to a voltage source in accordance with the present invention.

An alternative embodiment of the heated stylet, now designated 76', is shown in FIG. 21, which is a cross-sectional view similar to the view depicted in FIG. 19. The length of the stylet 76' is such that it is shown broken. This embodiment is suitable for transferring heat where the conductor wire 42 is separately insulated and cannot be used to complete a circuit with the voltage source 90. Here, the stylet 76' consists of a conducting wire bent into two parallel sections partially coated by the coating, now designated 88', so as to form a conducting loop 92 distally. The voltage source 90 is coupled across the proximal ends 94 of the stylet 76' to complete the circuit.

The foregoing illustrated embodiments include two adjoining shapememory segments 28 and 30. However, the person of ordinary skill in the art will appreciate that there is a myriad of possible arrangements for the sleeve 12. For example, the sleeve 12 may be provided with a single segment, such as 28, connected at either end to a non-shape-memory segment like the segment 26. Alternatively, another non-shape-memory segment like the segment 26 may be interposed between two shape-memory segments, such as 28 and 30. A given segment, such as 28, may be located anywhere along the length of the sleeve 12 where an in situ deformation is desired. In addition, the entire sleeve 12 may be fabricated from a shape-memory polymeric material. These examples illustrate just a few of the possibilities contemplated in accordance with the present invention.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents and alternatives falling within the spirit and scope of the invention as defined by the following appended claims.

What is claimed is:

1. A cardiac lead, comprising:
   a connector for coupling to a cardiac stimulator;
   a flexible tubular sleeve coupled to the connector, the sleeve being composed of a thermally-sensitive shape-memory polymeric material, the sleeve being deformable in situ into a permanent shape;
   a first electrode coupled to the sleeve; and
   a conductor wire coupled to the connector and to the first electrode.

2. The cardiac lead of claim 1, comprising a second electrode coupled to the sleeve and a second conductor coupled to the second electrode and the connector.

3. The cardiac lead of claim 1, comprising a tubular segment of non-shape-memory polymeric material coupled between the first electrode and the sleeve.

4. The cardiac lead of claim 1, comprising a tubular segment of non-shape-memory polymeric material coupled between the connector and the sleeve.

5. The cardiac lead of claim 1, comprising a tine coupled to the sleeve and being composed of a shape-memory polymeric material and being deformable in situ into a permanent radially outwardly projecting shape.

6. The cardiac lead of claim 5, wherein the tine has a lumen to enable fluid to pass through the tine.

7. The cardiac lead of claim 5, wherein the sleeve has a passage to enable fluid injected into the sleeve to exit the sleeve and pass over the tine.

8. The cardiac lead of claim 5, wherein the tine is deformable in situ into a permanent radially outwardly projecting hook shape.

9. A cardiac lead, comprising:
   a connector for coupling to a cardiac stimulator;
   a tubular sleeve coupled to the connector, the sleeve having a first segment composed of a thermally-sensitive shape-memory polymeric material and a second segment of a non-shape-memory polymeric material, the first segment being deformable in situ into a first permanent shape;

a first electrode coupled to the sleeve; and a conductor wire coupled to the connector and to the first electrode.

10. The cardiac lead of claim 9, comprising an elongated rib coupled to the first segment and being composed of a thermally sensitive shape-memory polymeric material and being deformable in situ into a second permanent shape.

11. The cardiac lead of claim 9, comprising an elongated rib coupled to the second segment and being composed of a thermally sensitive shape-memory polymeric material and being deformable in situ into a second permanent shape.

12. The cardiac lead of claim 9, wherein the first electrode is coupled to the second segment.

13. The cardiac lead of claim 9, comprising a second electrode coupled to the sleeve.

14. The cardiac lead of claim 13, wherein the second electrode is coupled to the first segment.

15. The cardiac lead of claim 9, wherein the sleeve comprises a third segment coupled to the first segment and being composed of a thermally-sensitive shape-memory polymeric material.

16. The cardiac lead of claim 15, wherein the first segment has a greater glass transition temperature than the third segment.

17. The cardiac lead of claim 15, comprising a first radiographic marker coupled to the first segment and a second radiographic marker coupled to the third segment.

18. The cardiac lead of claim 9, wherein the tine has a lumen to enable fluid to pass through the tine.

19. The cardiac lead of claim 9, wherein the sleeve has a passage to enable fluid injected into the sleeve to exit the sleeve and pass over the tine.

20. The cardiac lead of claim 9, wherein the tine is deformable in situ into a permanent radially outwardly projecting hook shape.

21. A cardiac lead, comprising:

a connector for coupling to a cardiac stimulator;

a tubular sleeve coupled to the connector, the sleeve having a first segment composed of a thermally-sensitive shape-memory polymeric material and a second segment disposed over and coupled to the first segment, the second segment being composed of a thermally-sensitive shape-memory polymeric material, the first and second segments being deformable in situ into a first permanent shape and second permanent shape;

a first electrode coupled to the sleeve; and a conductor wire coupled to the connector and to the first electrode.

22. The cardiac lead of claim 21, wherein the first segment has a greater glass transition temperature than the second segment.

23. The cardiac lead of claim 21, wherein the second segment has a greater glass transition temperature than the first segment.

24. A cardiac lead, comprising:

a connector for coupling to a cardiac stimulator;

a flexible tubular sleeve coupled to the connector and having a lumen, the sleeve being composed of a thermally-sensitive shape-memory polymeric material, the sleeve being deformable in situ into a permanent shape;

a first electrode coupled to the sleeve;

a conductor wire coupled to the connector and to the first electrode; and a stylet removably disposed in the lumen, the stylet being adapted to transfer heat to the sleeve in situ.

25. The cardiac lead of claim 24, wherein the stylet has a proximal end having an electrically insulating coating and a distal end having a reduced diameter portion and a radially outwardly projecting portion adapted to make electrical connection with the conductor wire.

26. The cardiac lead of claim 25, comprising a voltage source coupled to one end of the stylet and to the connector.

27. The cardiac lead of claim 24, wherein the stylet comprises a half-loop having first and second proximal ends and a distal portion, the distal portion being disposed in the lumen.

28. The cardiac lead of claim 27, comprising a voltage source coupled to the first and second proximal ends of the half-loop.

29. The cardiac lead of claim 25, comprising a tine coupled to the sleeve and being composed of a shape-memory polymeric material and being deformable in situ into a permanent radially outwardly projecting shape.

30. The cardiac lead of claim 29, comprising an annular member disposed in the lumen and being coupled to the sleeve, the annular member having an inner diameter smaller than the stylet to prevent the stylet from passing through the annular member.

31. The cardiac lead of claim 29, wherein the tine has a thermally conducting filament disposed therein to conduct heat from the stylet to the tine.

32. The cardiac lead of claim 29, wherein the tine is deformable in situ into a permanent radially outwardly projecting hook shape.

* * * * *